July 28, 1942. D. W. ULERY Plant Pat. 535
SAINTPAULIA PLANT
Filed Jan. 26, 1942
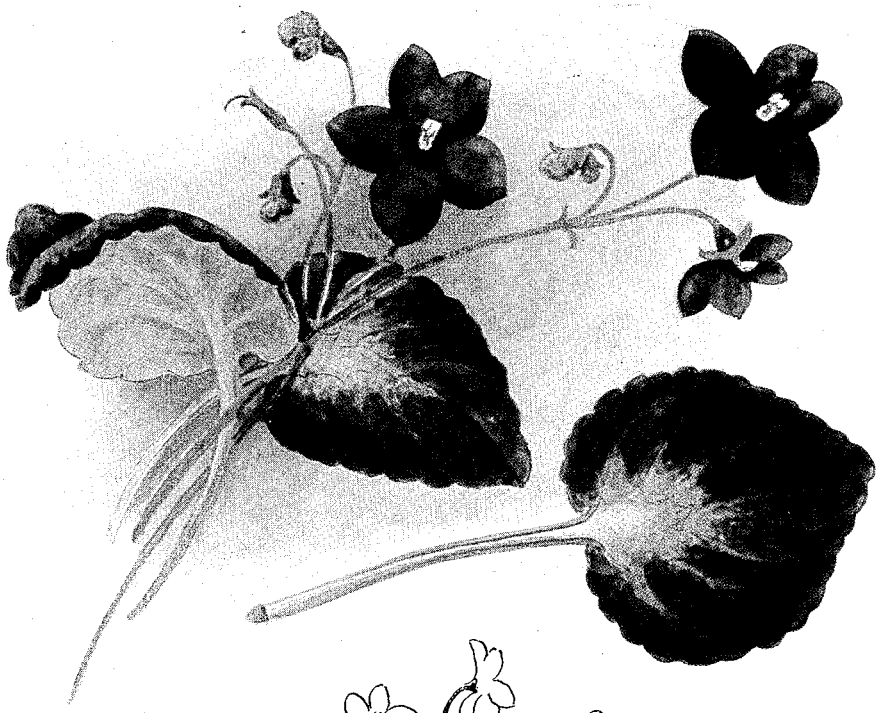
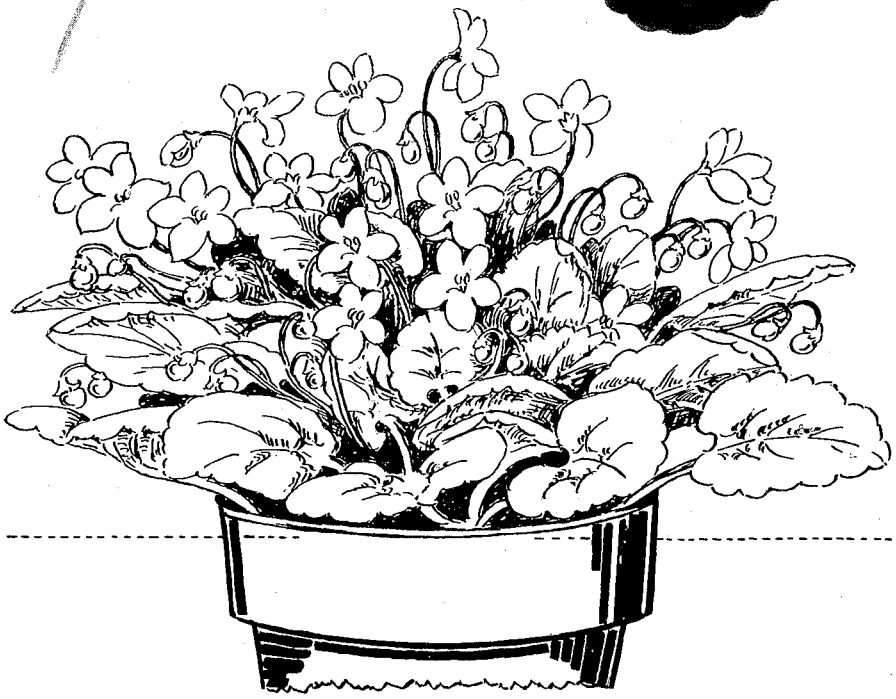
WITNESS:
Addison E. Avery
INVENTOR:
Dale W. Ulery,
by
Kummler, Kummler & Davis,
ATTORNEYS.

Patented July 28, 1942

Plant Pat. 535

UNITED STATES PATENT OFFICE

535

SAINTPAULIA PLANT

Dale W. Ulery, Springfield, Ohio, assignor to Ulery Greenhouses, Springfield, Ohio, a partnership composed of Orville B. Ulery, Carl J. Ulery, and Dale W. Ulery Application January 26, 1942, Serial No. 428,267

1 Claim. (Cl. 47—60)

The present discovery relates to improvements in Saintpaulia plants and consists of a new and distinct variety of *Saintpaulia ionantha grandiflora* Hort., which is a mutational variation from the well-known variety "Blue Boy."

Asexual reproduction of this new variety by cuttings since 1938 has shown its qualities to be permanently fixed. The principal object in carrying on this reproduction was to propagate an improved "Blue Boy" Saintpaulia which would be a hardy, ornamental plant with a profusion of blooms and well adapted for marketing.

The new Saintpaulia plant is distinguishable from the parent plant mainly in the color, form and growing habit of its velvety green leaves.

It is identical with the well-known Saintpaulia "Blue Boy" in shape and color of its flowers.

This new plant differs from other known Saintpaulia plants in the following respects:

The leaf is shorter and heart-shaped, instead of elongated.

The leaf has a scalloped or round-crested serrated edge which becomes more pronounced with the age of the plant.

The petioles are shorter, and more sturdy than "Blue Boy," and leave the crown at an upward angle, thus carrying the leaf above the pot and preventing it from bending downward. This feature makes the plant easier to handle and facilitates wrapping for shipment, with less danger of breaking the foliage.

Each leaf has a pronounced, ivory-colored, heart-shaped spot at its axil. From this light veinings of a delicate shade of green blend into the rich velvety darker green of the body of the leaf.

The leaf stem or petiole is triangular, the flat side uppermost, with a veining of red following the outside angles of the stem up to the ivory variegation of the leaf. This rare combination of colors of the leaves and stems gives the plant a highly decorative appearance, even when it is not in bloom.

As the petioles are short and the peduncles and pedicels of the flowers very sturdy, this new variety carries the blooms well above the foliage. This habit of growth is so distinctive that it increases the value of this species as a potted or house plant.

The foliage of this new plant is a lighter shade of green that "Blue Boy" and this characteristic, together with the ivory variegation, permits it to take more sunlight in growing and to require less shading. This is a distinct advantage in developing a house plant.

This new variety of Saintpaulia is a very free bloomer, which is true of the small-sized plants as well as the mature ones. One of its desirable characteristics is its ability to produce an unusually large number of blossoms—3 to 5 buds and blooms to each peduncle.

The accompanying illustration shows, in full color, a cluster of flowers and the leaves, and below a pen and ink sketch of the plant as a whole. The broken horizontal reference line helps one to visualize the upstanding disposition of the leaf stems.

The novelty of color, shape and upward trend of the leaves which are supported on red striped petioles is of primary importance and together with the profusion of violet-colored flowers with their brilliant yellow stamens, the trim well-proportioned form of the plant, and superior keeping qualities, all contribute to make a very desirable and choice commercial product.

The following is a detailed description of the new variety:

Parentage: Sport.
Parent variety: "Blue Boy."
Classification: Botanic.
*Saintpaulia ionantha grandiflora Hort.*

*Flower*

Blooming habit: Recurrent and continuous.
Bloom:
*Size.*—1⅛ inches.
*Borne.*—Clusters, 3 to 5.
*Stems.*—Sturdy, erect.
*Petalage.*—5.
*Color.*—Shade of blue-violet.
*Discoloration.*—None.
*Texture.*—Good.
*Affected by wet or hot weather.*—No.
*Persistence.*—(Hang on and dry)—10 days.
*Lasting qualities.*—Very good.
Genital organs:
*Stamens.* — Length — short. Number — 2 arched toward each.
*Anthers.*—Color—bright yellow. Arrangement—side by side in abutting bilobate pairs.
*Pistil.*—Number—1. Length—short.
*Ovaries.*—Single with many ovules.

*Plant*

Form: Rosette.
Foliage:
*Height.*—About 4 inches.
*Quantity.*—Bushy.
*Color.*—New foliage—green with ivory-colored spot at axil of leaf.
*Size of leaf.*—2 x 2 inches.
*Texture.*—Heavy and hairy.
*Shape.*—Cordate with rounded scalloped edge.

The color designations according to "A Dictionary of Color by Maerz and Paul" are as follows:

| | Color | Plate | Letter | No. |
|---|---|---|---|---|
| Blossom: | | | | |
| Main body color of flower | | 42 | L | 11 |
| Stamens | | 10 | L | 3 |
| Large buds | Starflower | 43 | G | 3 |
| Bud calyx | Auburn | 7 | C | 11 |
| Penduncles | | 6 | I | 9 |
| Leaf: | | | | |
| Body of leaf | | 23 | L | 7 |
| Spot at axil of leaf | | 17 | D | 1 |
| Veins from ivory-colored stop to body of leaf | Calliste Gr. | 19 | L | 6 |
| Red-colored stripes on sides of triangular leaf stem | | 46 | L | 1 |
| Underside of leaf | | 18 | E | 4 |

Having thus disclosed my invention, I claim:

A new and ornamental variety of Saintpaulia plant, characterized particularly by its vigorous growth; prolific production of blossoms; sturdy stems; the distinctive pattern and color, ivory-colored spot at the axil, of its leaves with scalloped edges; and the upward trend in growth of the leaves which are borne on triangular-shaped petioles whose outer edges are marked with red stripes, substantially as described.

DALE W. ULERY.